United States Patent [19]

Anderson

[11] 4,158,096

[45] Jun. 12, 1979

[54] INTERMEDIATES FOR INSECT PHEROMONE

[75] Inventor: Richard J. Anderson, Palo Alto, Calif.

[73] Assignee: Zoecon Corporation, Palo Alto, Calif.

[21] Appl. No.: 886,326

[22] Filed: Mar. 13, 1978

[51] Int. Cl.² ............... C07C 33/02; C07C 43/30; C07C 69/16
[52] U.S. Cl. ............... 560/262; 260/348.57; 260/348.58; 260/456 R; 560/248; 560/261; 568/598; 568/840; 568/857; 424/84
[58] Field of Search ............... 560/262; 568/840, 857, 568/598; 260/615 A

[56] References Cited

U.S. PATENT DOCUMENTS

| | | | |
|---|---|---|---|
| 2,669,579 | 2/1954 | Urban | 560/262 |
| 3,919,329 | 11/1975 | Anderson et al. | 260/615 A |
| 3,927,030 | 12/1975 | Demole | 568/857 |
| 3,948,814 | 4/1976 | de Rijke | 260/615 A |
| 4,014,942 | 3/1977 | Labovitz et al. | 560/262 |
| 4,059,641 | 11/1977 | Mishima et al. | 568/857 |

OTHER PUBLICATIONS

Roelofs et al., Nature 267, 698, Jun. 23, 1977.

*Primary Examiner*—Vivian Garner
*Attorney, Agent, or Firm*—Donald W. Erickson

[57] ABSTRACT

Synthesis and intermediates for making insect pheromone useful in the control of red scale, *Aonidiella aurantii*.

6 Claims, No Drawings

INTERMEDIATES FOR INSECT PHEROMONE

This invention relates to the synthesis of a component of the sex pheromone of the California red scale, *Aonidiella aurantii* (Maskell) and intermediates therefor.

The California red scale is a pest of citrus. The natural female pheromone attracting the male red scale consists of 3-methyl-6-isopropenyl-9-decen-1-yl acetate (AI) and (Z)-3-methyl-6-isopropenyl-3,9-decadien-1-yl acetate (AII). Roelofs et al., Nature 267, 698 (June 23, 1977). Most of the activity of compound AI appears to be associated with the 3S,6RS enantiomers.

The synthesis of the present invention can be outlined as follows.

anhydride in pyridine or the like to obtain only hydroxy acetate (V, R is acetyl). The hydroxy acetate is converted to the mesylate and then treated with base such as triethylamine or diazabicyclo[2.2.2]octane to obtain the diene AI. Along wtih the diene AI is formed some of the diene (A'I).

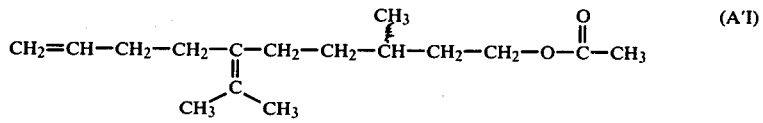

The diene (A'I) is easily separated from the mixture of diene AI and A'I by selective epoxidation using, for example, m-chloroperbenzoic acid. The epoxide (A'I) which is more polar is then separated by chromatography.

The synthesis described above is applicable to forming AI as the 3S-enantiomer, 3R-enantiomer or mixture, such as a racemic mixture, of 3R,S-enantiomers depending on whether the starting material III is the l- or d-

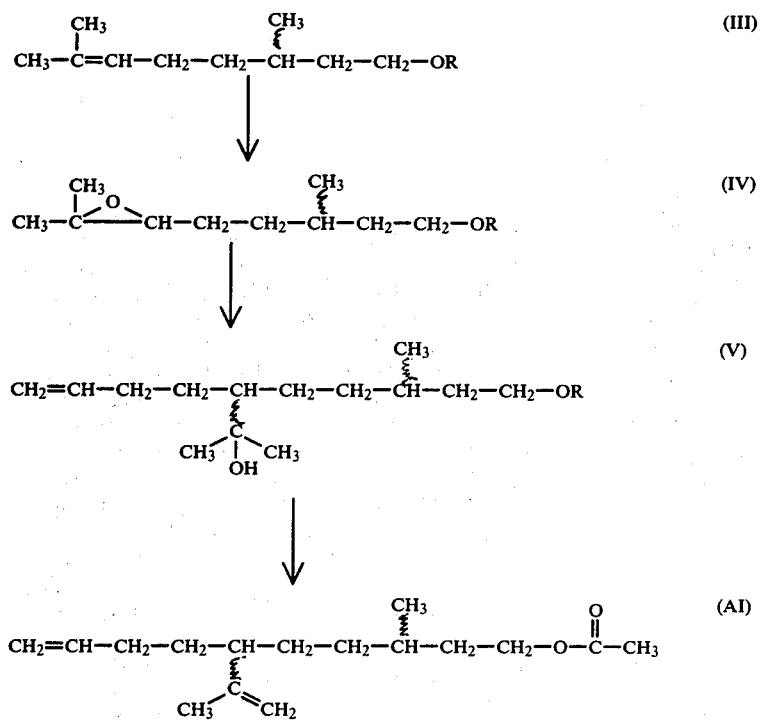

In the practice of the above synthesis, citronellyl acetate (III, R is acetyl) is epoxidized to form the 6,7-epoxide (IV) using m-chloroperbenzoic acid or the like in dichloromethane. The wavy line at C-3 denotes the d- or l-enantiomer or a mixture (dl) of enantiomers. The epoxide IV is reacted with di(3-buten-1-yl)lithium cuprate to form the diol (V, R is hydrogen) and the hydroxy acetate (R is acetyl). The wavy line at C-6 denotes a mixture of R and S enantiomers. The mixture of diol and hydroxy acetate V is acetylated using acetic enantiomer or a mixture of dl-enantiomers. The compound AI as the 3R-enantiomer appears to have a lower level of attractancy. In the preferred practice, the starting material III is the l-enantiomer or racemic d,l-enantiomers. The separation of AI into the 6R and 6S enantiomers, which is not easily done, appears unnecessary for maintaining attractancy of AI.

In another embodiment of the synthesis, the 2,5-dioxahexyl ether of citronellyl alcohol is used as the starting material. The synthesis can be outlined as follows.

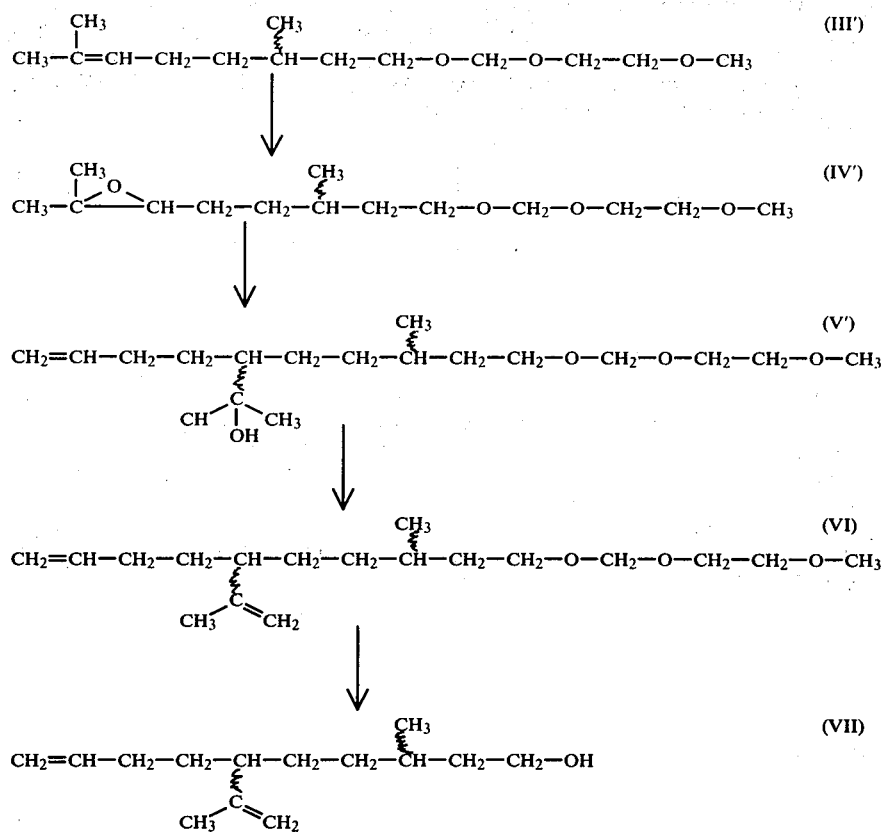

In the practice of the above outlined synthesis, d- or 1-citronellol or dl-citronellol is reacted with 2,5-dioxahexyl chloride and n-butyl lithium to form the ether (III'). The ether is reacted with m-chloroperbenzoic acid to form the 6,7-epoxide (IV') which is reacted with di(3-buten-1-yl)lithium cuprate to form the hydroxy ether (V'). The hydroxy ether is treated with methanesulfonyl chloride followed by base to form the di-substituted olefin (VI). Some tetra-substituted olefin is formed which can be separated out as the epoxide now by the procedure as described hereinabove, or separated later. The di-substituted olefin VI is converted to the alcohol VII by treatment with n-butyl lithium followed by trichloroacetic acid. The alcohol VII is then acetylated using acetic anhydride in pyridine to obtain the desired acetate AI.

The following examples are provided to illustrate the practice of the present invention. Temperature is given in degrees Centigrade.

EXAMPLE 1

To 15.6 g (0.1 mol) dl-citronellol in 20 ml of dry pyridine under nitrogen is added 11.3 ml (0.12 mol) of acetic anhydride. The reaction is stirred about 48 hours and then ice is added. After one hour, the reaction is poured into hexane and water. The organic phase is washed with 5% HCl, 2M sodium carbonate, and saturated NaCl solutions, dried over calcium sulfate and solvent removed to yield dl-citronellyl acetate.

To 19.15 g (0.097 mol) of dl-citronellyl acetate in 150 ml of dichloromethane at 0° is added 21.3 g (0.105 mol) of m-chloroperbenzoic acid (85%) in portions. The reaction mixture is stirred for about 18 hours and then filtered. The solids are washed with dichloromethane. The combined dichloromethane washings and filtrate are then washed with sodium sulfite solution, 2M sodium crbonate, and sat. NaCl solution, dired over calcium sulfate and solvent removed to yield 6,7-epoxide of dl-citronellyl acetate.

Lithium metal wire (2.18 g), washed in pentane, in short pieces is put into 50 ml of ether and 4-chloro-1-butene (14.25 g) under argon. The mixture is allowed to warm to room temperature briefly and then returned to ice-bath and stirred for about 3.5 hours. To cuprous iodide (8.57 g) in 50 ml of ether, under argon, the thus-prepared lithium reagent (91 mmol) is added slowly with the temperature at about −20°. After addition is complete, the reaction mixture is allowed to stand for 2.5 hours. Additional ether (about 60 ml) is added followed by 3.5 g of 6,7-epoxide of dl-citronellyl acetate in ether at about −10°, under argon. The reaction mixture is stirred at about 4° for 18 hours and then worked up by partitioning between ether/ammonium sulfate which is filtered through Celite. The ether layer is separated, washed with ammonium sulfate and brine, dried over sodium sulfate and rotoevaporated to yield a mixture of the diol, 3-methyl-6-(2'-hydroxypropan-2'-yl)-9-decen-1ol, and the C-1 acetate thereof.

The mixture of diol and C-1 acetate (6.04 g) is reacted with acetic anhydride (3.35 g) in pyridine as above to convert the mixture to only the C-1 acetate of 3-methyl-6-(2'-hydroxypropan-2'-yl)-9-decen-1-ol.

To 0.51 g of the above C-1 acetate in 3 ml of dichloromethane, under nitrogen, at −5°, is added diazabicyclo[2.2.2]octane (0.76 g), with stirring, followed by 0.22 of methanesulfonyl chloride. Additional diazabicyclo[2.2.2]octane (0.26 g) and methanesulfonyl chloride (0.2 ml) are added at 0° with stirring and allowed to stand overnight. The reaction is worked up in water/ether. The ether phase is washed with water and brine, dried over sodium sulfate and solvent removed to yield a mixture of 3-methyl-6-isopropenyl-9-decent-1-yl acetate and 3-methyl-6-(isoprop-2'-enyl)-9-decen-1-yl acetate.

To 0.30 g of the above mixture of di-olefins and 2.5 ml of chloroform, under nitrogen at 0°, with stirring, is added 0.046 g of m-chloroperbenzoic acid (85%). After about 6 hours, the reaction is worked up in ether/sodium bisulfite. The ether phase is washed with water and brine, dried over sodium sulate and rotoevaporated. The product is purified by plating on preparatory thin layer chromatography plates (Rhodamine impregnated) eluting with 5% ether/hexane followed by distillation to give the racemic (3RS, 6RS) 3-methyl-6-isopropenyl-9-decan-1-yl acetate, b.p. 75° (0.08 mm Hg.).

EXAMPLE 2

Following the procedure of Example 1, 1-6,7-epoxycitronellyl acetate is prepared by the reaction of m-chloroperbenzoic acid and 1-citronellyl acetate which is reacted with di(3-butenyl)lithium cuprate to form a mixture of 3-methyl-6-(2'-hydroxypropan-2'-yl)-9-decen-1-yl acetate and 3-methyl-6-(2'-hydroxypropan-2'-yl)-9-decen-1-ol (each compound is the S isomer at C-3). The mixture is treated with acetic anhydride as above to form C-1 acetate only. The C-1 acetate (0.64 g) is dissolved in dichloromethane (about 10 ml) and cooled in acetone/dry-ice bath. Then 0.75 ml (5.4 mmol) of triethylamine is added followed by 0.20 ml of methanesulfonyl chloride. The reaction mixture is allowed to warm to room temperature and stand overnight. The reaction is poured into water and then separated and the aqueous phase extracted with dichloromethane. The organic phases are combined, washed with water and brine, dried over sodium sulfate, filtered and solvent evaporated. The reaction product (mixtue of olefins) is treated with 0.10 g of 85% m-chloroperbenzoic acid in dichloromethane at 0°, under nitrogen. After about 1.5 hours, the reaction is quenched with sat. sodium bisulfite and extracted with ether. The organic phases are combined, washed with sodium bisulfite, potassium carbonate and sodium chloride solutions, dried, filtered and evaporated. The reaction product is plated by prep. thin layer chromatography plates eluting with 10% ether/hexane, to give (3S, 6RS) 3-methyl6-isopropenyl-9-decen-1-yl acetate, b.p. 80-85° (0.8 mm Hg.).

EXAMPLE 3

To a solution of 1-citronellol (14.41 g) and 50 ml of tetrahydrofuran, cooled to $-78°$, under nitrogen, is slowly added 60 ml of 1.6M n-butyl lithium while maintaining temperature below $-35°$. The reaction mixtutre is allowed to warm to $-10°$ and then 11 ml of 2,5-dioxahexyl chloride is added slowly. The reaction mixture is allowed to warm to room temperature and then is stirred about 16 hours at room temperature, under nitrogen. The reaction is quenched with water and partitioned between water/ether. Aqueous phase is extracted with ether and the ether extracts combined with the ether phase. The combined ether portion is washed with water and brine, dried over sodium sulfate and solvent evaporated to give the 2,5-dioxahexyl ether of 1citronellol (22.76 g).

To a mixture of the 2,5-dioxahexyl ether of 1-citronellol (22.76 g) and about 250 ml of dichloromethane, cooled in an ice bath, under nitrogen, with stirring, is added m-chloroperbenzoic acid (19.50 g) over above 40 minutes. The reaction is allowed to warm to room temperature. The reaction is worked up by partitioning between ether/sat. sodium bisulfite - 2N sodium carbonate. The aqueous phase is back extracted with ether. The combined ether phase is washed with sodium bisulfite, sodium carbonate and brine, dired over sodium sulfate and evaporated to yield the 6,7-epoxide of 2,5-dioxahexyl 1-citronellyl ether (23.81 g).

EXAMPLE 4

To lithium di(3-buten-1yl)cuprate in ether (13.02 mmol), prepared as in Example 1, at about $-10°$, is added 1.1 g of the 6,7-epoxide of 2,5-dioxahexyl 1-citronellyl ether (4.22 mmol). The reaction mixture is stirred at about 4° for about 16 hours. The reaction is worked up in ether/water, washed with ammonium sulfate and brine, dired over sodium sulfate and solvent evaporated. Reaction product is plated on prep. thin layer chromatography plates eluting with 35% ethyl acetate/hexane to yield 2,5-dioxahexyl(3S, 6RS)-3-methyl-6-(2'-hydroxypropan-2'-yl)-9-decen-1-yl ether (yield 0.92 g).

To 0.77 g (1.98 mmol) of the above hydroxy ether in about 15 ml of dichloromethane, at 0°, under nitrogen, is added triethylamine (1.0 g, 9.88 mmol) followed by slow addition of methanesulfonyl chloride (0.68 g, 5.93 mmol). The reaction is allowed to warm to room temperature and then worked up in ether/sodium carbonate solution. The ether phase is washed with dilute HCL, water, sodium carbonate, water and brine, dried over sodium sulfate and evaporated. The product is plated on prep. thin layer chromatography plates eluting with 25% ether/hexane to yield 2,5-dioxahexyl(3S,6RS)-3-methyl-6-isopropenyl-9-decen-1-yl ether (0.591 g) and some tetra-substituted olefin which can be removed by selective epoxidation followed by thin layer or column chromatography.

To a solution of the above di-substituted olefin (0.38 g, 1.27 mmol) in 5 ml of hexane is added one equivalent of n-butyl lithium (1.6M), and the mixture stirred for about one hour, under nitrogen, at room temperature. Thin layer chromatography shows starting material present. Then 4.5 equivalents of n-butyl lithium are added and stirring continued for about 6 hours at room temperature. The reaction is quenched with water and extracted with ether. The ether extracts are combined, washed with brine, dried over magnesium sulfate and solvent removed. The residue is dissolved in 8 ml tetrahydrofuran and 2 ml water and adjusted to acid pH with trichloroacetic acid. The mixture is heated at 65°, under nitrogen, for about 2 hours, and then allowed to cool. The reaction is worked up by adding small amount of NaCl and partitioning between brine/ether. The combined ether extracts are washed with sodium carbonate and brine, dried over magnesium sulfate and evaporated to yield (3S,6RS)-3-methyl-6-isopropenyl-9-decen-1-ol (0.278 ).

What is claimed is:

1. A compound of the formula:

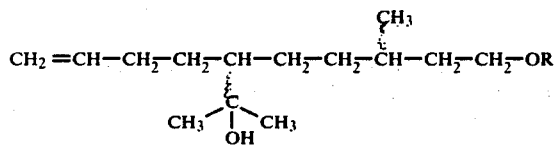
in which R is hydrogen, acetyl or 2,5-dioxahexyl.
2. A compound of claim 1 wherein R is acetyl.
3. The 3S,6RS enantiomers of the compound according to claim 2.
4. A compound of claim 1 wherein R is 2,5-dioxahexyl.
5. The 3S,6RS enantiomers of the compound according to claim 4.
6. The compound, 2,5-dioxahexyl-3-methyl-6-1-isopropenyl-9-decen-1-yl ether.
* * * * *